(12) United States Patent
Tanaka et al.

(10) Patent No.: US 8,167,144 B2
(45) Date of Patent: May 1, 2012

(54) WATER SEPARATION MEMBRANE

(75) Inventors: Akihisa Tanaka, Wako (JP); Kazuhiro Kagawa, Wako (JP); Pu Qian, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 259 days.

(21) Appl. No.: 12/502,546

(22) Filed: Jul. 14, 2009

(65) Prior Publication Data

US 2010/0006496 A1   Jan. 14, 2010

(30) Foreign Application Priority Data

Jul. 14, 2008 (JP) ................................ 2008-182867
Apr. 3, 2009 (JP) ................................ 2009-091492

(51) Int. Cl.
*B01D 71/62* (2006.01)
*B01D 71/26* (2006.01)
*B01D 71/82* (2006.01)
*B01D 71/00* (2006.01)

(52) U.S. Cl. ......... 210/500.37; 210/500.41; 210/500.42; 210/500.33

(58) Field of Classification Search ........................ None
See application file for complete search history.

(56) References Cited

U.S. PATENT DOCUMENTS

| 5,096,586 | A * | 3/1992 | Kaner et al. | 210/500.37 |
| 6,258,271 | B1 * | 7/2001 | Jitariouk et al. | 210/500.23 |
| 2004/0099597 | A1 * | 5/2004 | Jitariouk et al. | 210/321.79 |
| 2009/0001009 | A1 * | 1/2009 | Linder et al. | 210/243 |

FOREIGN PATENT DOCUMENTS

| JP | 7-185275 | 7/1995 |
| JP | 2006-88136 | 4/2006 |

* cited by examiner

*Primary Examiner* — Krishnan S Menon
(74) *Attorney, Agent, or Firm* — Nelson Mullins Riley & Scarborough LLP; Anthony A. Laurentano

(57) ABSTRACT

Provided is a water separation membrane capable of effectively separating water from a water solution of ethanol, saccharide or the like. The water separation membrane is composed of polypyrrole doped with a sulfonate ion. The sulfonate ion may be an aromatic or aliphatic sulfonate ion.

3 Claims, 2 Drawing Sheets

WATER SEPARATION MEMBRANE

BACKGROUND OF THE INVENTION

1. Field of the Invention

The present invention relates to a water separation membrane for separating water from a water solution of ethanol, saccharide or the like.

2. Description of the Related Art

In recent years, from the viewpoint of preventing global warming, it has been called on to reduce emission amount of carbon dioxide which is considered to be one of the reasons of global warming. Therefore, there has been considered to use a mixed fuel of ethanol and a liquid hydrocarbon compound such as gasoline as a vehicle fuel. The ethanol can be yielded from fermentation of a plant material, for example, an agricultural crop such as sugar cane, corn or the like. Since the plant itself, the raw material of the plant material, has absorbed carbon dioxide via photosynthesis, even though the ethanol produced from the plant material is combusted, the emission amount of carbon dioxide is equal to the amount of carbon dioxide absorbed by the plant itself. In other words, the summed emission amount of carbon dioxide can be made theoretically equal to zero, which is the so-called carbon neutral effect. Therefore, the emission amount of carbon dioxide can be reduced in accordance with the amount of ethanol which is used to replace the liquid hydrocarbon compound such as gasoline.

However, if sugar cane, corn and the like are consumed in a large amount as the raw materials of ethanol, there is a problem that the amount thereof supplied as food would be decreased.

In this regard, there has been considered a technology to produce ethanol by using an inedible biomass containing cellulose instead of the plant material, such as sugar cane, corn or the like. As examples of the biomass containing cellulose, wood, rice straw, haulm, bagasse, bamboo, pulp and waste materials originated therefrom, such as waste paper, may be given.

As a production method for ethanol, there has been known a method as disclosed, for example, in Japanese Patent Laid-open No. 2006-88136, in which the biomass containing cellulose is glycosylated by an enzyme to produce a saccharide solution, thereafter, the saccharide solution is fermented into an ethanol water solution by introducing therein ethanol fermentative bacteria.

However, the yielded ethanol water solution according to the mentioned production method is dilute, since the concentration of ethanol is ranged from 0.5 to 5.0 w %. Therefore, it is necessary to condensate it in order to be used as a liquid fuel. Generally, distillation method is adopted to perform the condensation treatment. However, when the concentration of ethanol reaches about 96 w %, ethanol and water are formed into an azeotrope; therefore, it is principally impossible to condensate the ethanol water solution further than 96 w % through the distillation method.

In this regard, there has been known a method as disclosed, for example, in Japanese Patent Laid-open No. H07-185275, in which ethanol is yielded in a concentration of more than 99 w % by separating water from the distilled ethanol water solution according to a pervaporation method. The pervaporation method adopts, for example, a zeolite water separation membrane to separate water from the ethanol water solution at a treatment temperature ranged from 50 to 75° C.

As the condensation treatment for the ethanol water solution, there also has been known a method to yield ethanol in a concentration of more than 99 w % through azeotropic distillation using benzene.

However, according to the condensation treatment for the ethanol water solution, either two steps of distillation and pervaporation are necessary or benzene is needed as an azeotropic compound, therefore, it is disadvantageous.

SUMMARY OF THE INVENTION

The present invention has been accomplished in view of the aforementioned problems, and it is therefore an object of the present invention to provide a water separation membrane capable of effectively separating water from a water solution of ethanol, saccharide or the like to yield the ethanol water solution, saccharide water solution or the like in high concentration.

To accomplish an object described above, the water separation membrane of the present invention is composed of a polypyrrole doped with a sulfonate ion.

By doping polypyrrole with sulfonate ion, the water separation membrane of the present invention can permeate water selectively. Therefore, according to the water separation membrane of the present invention, it is possible to yield ethanol water solution, saccharide water solution or the like in high concentration by effectively separating water from the water solution of ethanol, saccharide or the like.

In the water separation membrane of the present invention, the sulfonate ion may be an aromatic sulfonate ion or an aliphatic sulfonate ion. It is acceptable for the aromatic sulfonate ion to have a substituent group.

It is desirable for the aromatic sulfonate ion to have a benzene ring, and a naphthalene ring is preferable. Owning to the naphthalene ring included in the aromatic sulfonate ion, the water separation membrane of the present invention can permeate more water per unit surface area and unit time.

It is desirable for the aromatic sulfonate ion to have at least two sulfonate groups ($-SO_3^-$), preferably at least three sulfonate groups, as ionized sulfonic groups. Owning to at least the two sulfonate groups included in the aromatic sulfonate ion, the water separation membrane of the present invention can permeate further more water per unit surface area and unit time.

It is desired that the aliphatic sulfonate ion is a vinyl sulfonate ion. Owning to the fact that the aliphatic sulfonate ion is a vinyl sulfonate ion, the water separation membrane of the present invention can permeate more water per unit surface area and unit time.

It is preferable that the aliphatic sulfonate ion is a polyvinyl sulfonate ion. Owning to the fact that the aliphatic sulfonate ion is a polyvinyl sulfonate ion, the water separation membrane of the present invention can permeate further more water per unit surface area and unit time.

DETAILED DESCRIPTION OF THE PREFERRED EMBODIMENTS

Figure 1:
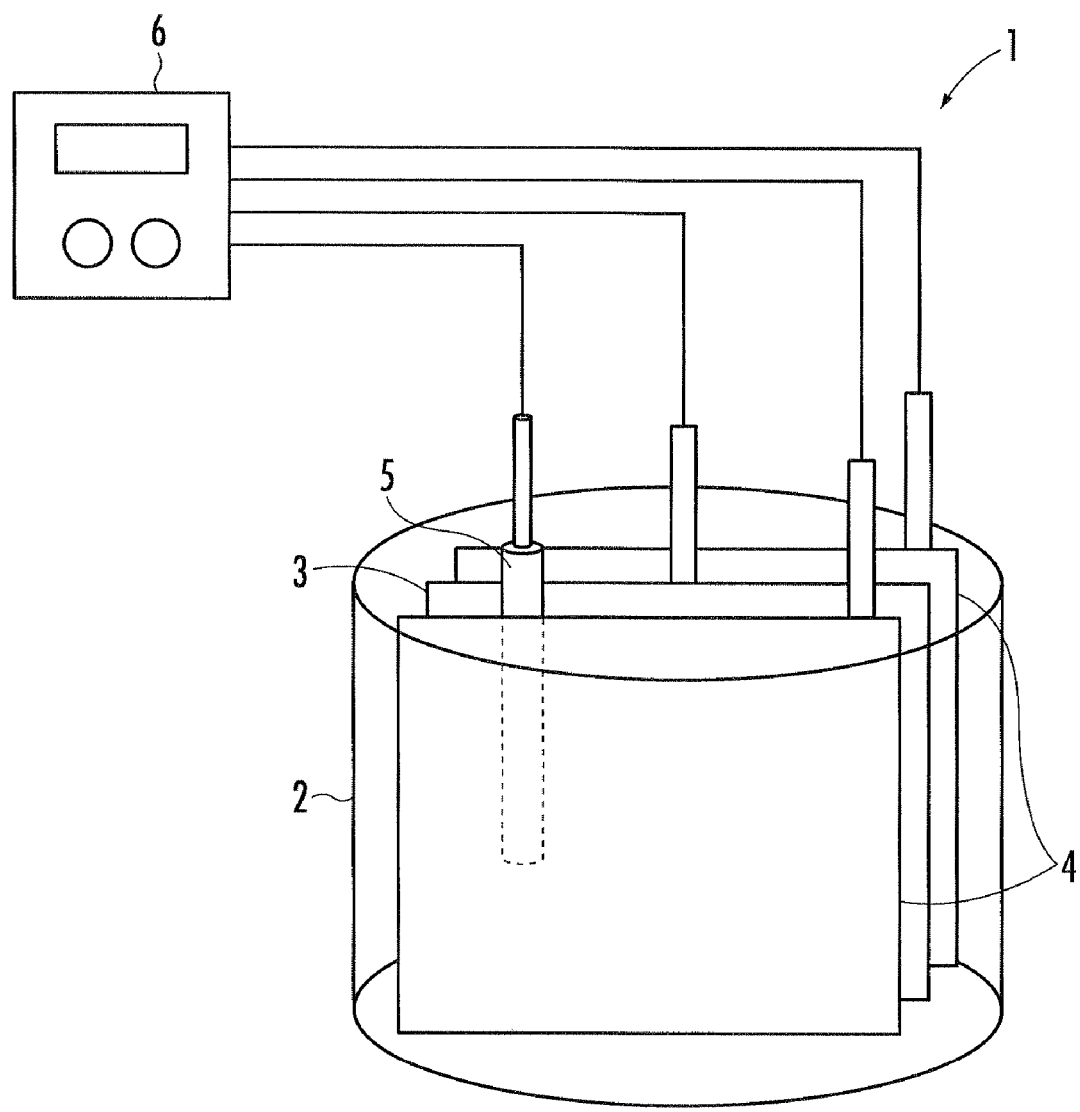
FIG. 1 is a structural view of a device used in manufacturing a water separation membrane of the present invention.

Hereinafter, an embodiment of the present invention will be described in detail.

A water separation membrane according to the present embodiment is composed of a polypyrrole doped with a sulfonate ion. Since polymers in the polypyrrole are bound with weak interacting Van der Waals force, it is easy for an ion to enter inside the polymers. Consequently, the polypyrrole can be doped by the sulfonate ion, which is an anion, under an oxidative condition. The polypyrrole doped with the sulfonate ion functions in the water separation membrane, selectively permeating water from a water solution of ethanol, saccharide or the like.

The sulfonate ion may be an aromatic sulfonate ion or an aliphatic sulfonate ion.

It is acceptable for the aromatic sulfonate ion to have a substituent group. It is desirable for the aromatic sulfonate ion to have a benzene ring or a naphthalene ring, and a naphthalene ring is preferable. It is favorable for the aromatic sulfonate ion to have at least two sulfonate groups (—$SO_3^-$), more favorably at least three sulfonate groups, as the ionized sulfonic groups.

As examples of the aromatic sulfonate ion, the following substances of chemical formulas (1) to (10) may be given.

Chemical Formulas (1) to (10)

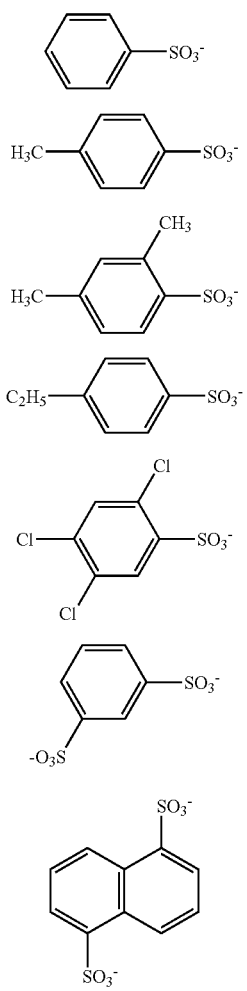

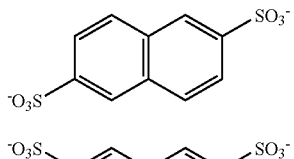

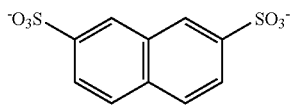

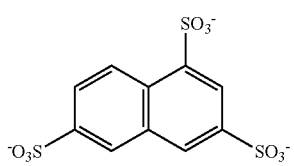

The aromatic sulfonate ion of chemical formula (1) is a benzene sulfonate ion, having a sulfonate group (—$SO_3^-$) in the benzene ring.

The aromatic sulfonate ion of chemical formula (2) is a p-toluene sulfonate ion, having a sulfonate group, and a p-methyl group relative to the sulfonate group as a substituent group in the benzene ring.

The aromatic sulfonate ion of chemical formula (3) is a 2,4-dimethyl benzene sulfonate ion, having a sulfonate group, and a p-methyl group and an o-methyl group relative to the sulfonate group as substituent groups in the benzene ring.

The aromatic sulfonate ion of chemical formula (4) is a 4-ethyl benzene sulfonate ion, having a sulfonate group and a p-ethyl group relative to the sulfonate group as a substituent group in the benzene ring.

The aromatic sulfonate ion of chemical formula (5) is a 2,4,5-trichloro benzene sulfonate ion, having a sulfonate group at position 1, and a chloro group at positions 2, 4 and 5, respectively, as a substituent group in the benzene ring.

The aromatic sulfonate ion of chemical formula (6) is a 1,3-benzene di-sulfonate ion, having a sulfonate group at positions 1 and 3, respectively, in the benzene ring.

The aromatic sulfonate ion of chemical formula (7) is a 1,5-naphthalene di-sulfonate ion, having a sulfonate group at positions 1 and 5, respectively, in the naphthalene ring.

The aromatic sulfonate ion of chemical formula (8) is a 2,6-naphthalene di-sulfonate ion, having a sulfonate group at positions 2 and 6, respectively, in the naphthalene ring.

The aromatic sulfonate ion of chemical formula (9) is a 2,7-naphthalene di-sulfonate ion, having a sulfonate group at positions 2 and 7, respectively, in the naphthalene ring.

The aromatic sulfonate ion of chemical formula (10) is a 1,3,6-naphthalene tri-sulfonate ion, having a sulfonate group at positions 1, 3 and 6, respectively, in the naphthalene ring.

As examples of the aliphatic sulfonate ion, the following substances of chemical formulas (11) and (12), respectively, may be given.

Chemical Formulas (11) and (12)

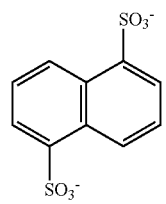

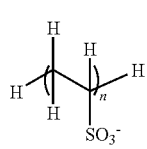

(12)

The aliphatic sulfonate ion of chemical formula (11) is a vinyl sulfonate ion, having a hydrogen atom in ethylene molecule substituted by the sulfonate group. The aliphatic sulfonate ion of chemical formula (12) is a polyvinyl sulfonate ion, having the vinyl sulfonate ion of chemical formula (11) as a constituent unit. In the chemical formula (12), the number n is desired to be in a range, for example, from 100 to 10,000.

It is desirable that the aliphatic sulfonate ion is the vinyl sulfonate ion having chemical formula (11). It is preferable that the aliphatic sulfonate ion is the polyvinyl sulfonate ion having chemical formula (12).

The water separation membrane of the present embodiment can be synthesized according to a constant-current oxidative polymerization method by using an electrochemical polymerization device 1 illustrated in FIG. 1, for example. The electrochemical polymerization device 1 includes a polymerization container 2, a working electrode 3, a pair of counter electrodes 4 and 4, and a reference electrode 5. All the electrodes are disposed inside the polymerization container 2. The counter electrodes 4 and 4 are disposed oppositely, having an equal distance to the working electrode 3. The reference electrode 5 is disposed between the working electrode 3 and one of the counter electrodes 4. The working electrode 3, the counter electrodes 4 and 4, and the reference electrode are electrically connected to a potentiostat 6, respectively.

The working electrode 3 is made of, for example, nickel plate. The surface thereof is ground evenly with an alumina abrasive. The counter electrodes 4 and 4 are made of a metal net, such as a nickel net.

To synthesize the water separation membrane according to the present embodiment, first, a sulfonic acid or a salt thereof corresponding to the sulfonate ion mentioned above, and pyrrole which is a monomer of polypyrrole are dissolved in a polymerization solvent to prepare a polymerization solution. As the polymerization solvent, for example, distilled water or ion-exchanged water is used. Pre-treatment on the polymerization solvent with argon gas or nitrogen gas to deaerate oxygen dissolved therein can contribute to an easy formation of the water separation membrane in high quality.

The concentration of the sulfonic acid or the salt thereof is in a range of 0.01 to 2.0 mol/L, for example. The concentration of the pyrrole in the polymerization solution is in a range of 0.01 to 2.0 mol/L, for example.

Subsequently, the polymerization solution is put into the polymerization container 2, the working electrode 3 is set as an anode and the counter electrodes 4 and 4 are set as a cathode, and the constant-current oxidative polymerization is performed at a current density, for example, in a range of 0.1 to 50 mA/cm² until a membrane of a predefined thickness is formed on both surfaces of the working electrode 3, respectively. The water separation membrane of the present embodiment is yielded by detaching the membranes formed on both surfaces of the working electrode 3 after the constant-current oxidative polymerization is completed.

Figure 2:
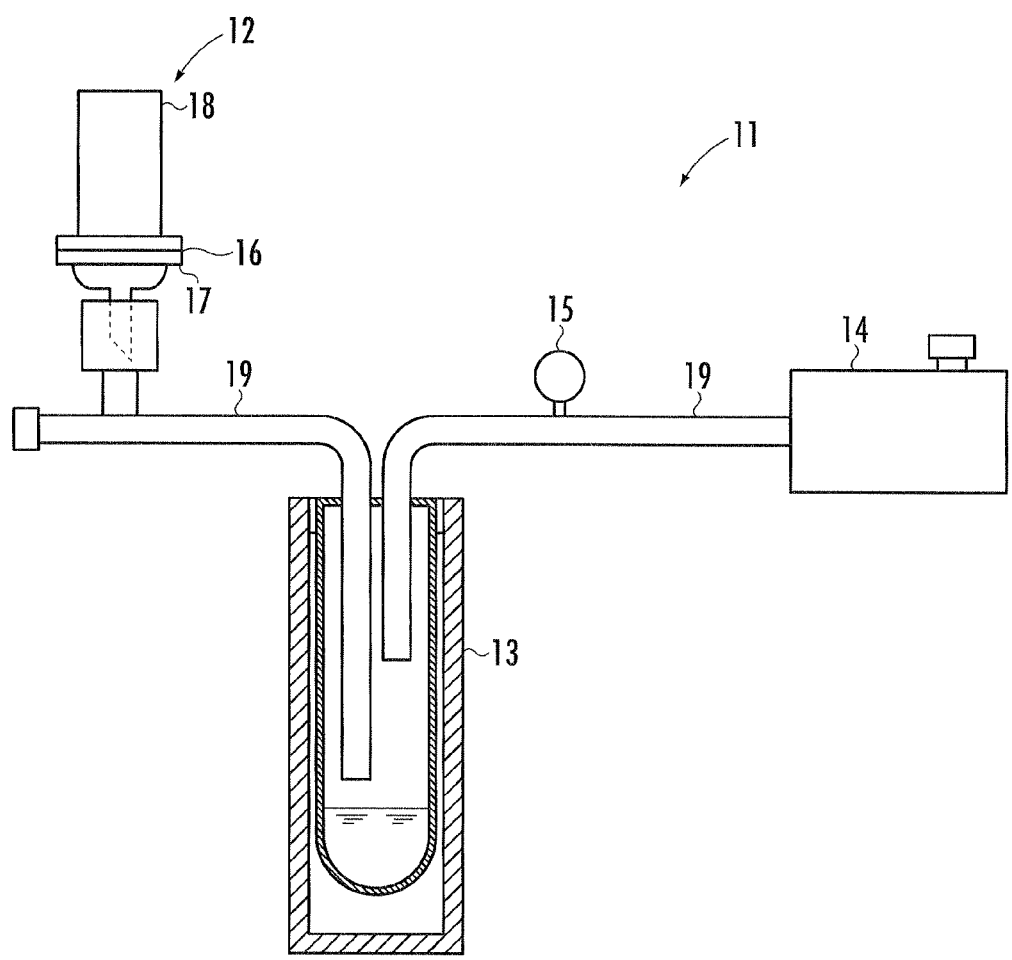
FIG. 2 is a structural view of a device used in pervaporation method.

The separation of water from water solution of ethanol, saccharide or the like by the water separation membrane of the present embodiment can be performed by using a pervaporation device 11 as illustrated in FIG. 2, for example.

The pervaporation device 11 illustrated in FIG. 2 is provided with a pervaporation cell 12, a cold trap 13 which is cooled by liquid nitrogen, a vacuum pump 14, and a vacuum indicator 15. The pervaporation cell 12 has a sintered circular glass filter 16, a filter holder 17, and a cylindrical supply member 18 disposed upper of the filer holder 17. A lower end portion of the filter holder 17 is connected with a conduit 19. The conduit 19 is connected to the vacuum pump 14 through the cold trap 13. The vacuum indicator 15 is disposed between the cold trap 13 and the vacuum pump 14.

The sintered circular glass filter 16 allows vapor to permeate and has an effective permeation area of 34.6 mm² (diameter 21 mm). The upper side of the sintered circular glass filter 16 is disposed with a toroidal sealing member (not shown) made from Parafilm (registered trademark). The water separation membrane is formed into a circular shape with a diameter equal to an outer diameter of the sealing member and is disposed on the sealing member.

The cylindrical supply member 18 is supplied with the water solution of ethanol, saccharide or the like as a treatment liquid. An inner circumferential side of the cylindrical supply member 18 is exposed with the water separation membrane.

The pervaporation treatment according to the pervaporation device 11 is performed by supplying the water solution of ethanol, saccharide or the like to the cylindrical supply member 18 as a treatment liquid, and the vacuum pump 14 is actuated to suction from the lower end portion side of the filter holder 17. As a result thereof, the condensed water solution of ethanol, saccharide or the like can be yielded in the cylindrical supply member 18 by selectively separating water from the water solution thereof. The separated water is trapped in the cold trap 13.

Hereinafter, examples of the present invention will be described.

Example 1

In the present example, firstly, ion-exchanged water is deoxidized by blowing argon gas therein. Next, a polymerization solution is prepared by dissolving 3.52 g of benzene sulfonic acid and then 1.34 g of pyrrole in 200 ml of the deoxidized ion-exchanged water. In the polymerization solution, the concentration of benzene sulfonate ion is 0.1 mol/L and the concentration of pyrrole is 0.1 mol/L.

Next, the polymerization solution prepared according to the present example was put into the polymerization container 2 of the electrochemical polymerization device 1 as illustrated in FIG. 1. The working electrode 3 was set as an anode and the counter electrodes 4 and 4 were set as a cathode, and the constant-current oxidative polymerization was performed at a current density of 0.2 mA/cm² for 3 hrs to yield a membrane of a thickness of roughly 10 μm on both surfaces of the working electrode 3, respectively. Thereafter, the water separation membrane composed of polypyrrole doped with benzene sulfonate ion of chemical formula (1) was yielded by detaching the membranes from the working electrode 3.

Thereafter, the water separation membrane yielded according to the present example was mounted in the pervaporation device 11 as illustrated in FIG. 2, and a water separation performance test was performed through pervaporation treatment.

In the water separation performance test, 3.93 g of 10 W % ethanol water solution was firstly supplied to the cylindrical supply member 18, then, the vacuum pump 14 was actuated to suction from the lower end portion side of the filter holder 17 for 3 hrs at room temperature (25° C.).

After the pervaporation treatment, the ethanol concentration of the ethanol water solution remained in the cylindrical supply member 18 and the ethanol concentration of the liquid trapped in the cold trap 13 were measured. According to the amount and the ethanol concentration of liquid trapped in the cold trap 13, water permeation rate ($g/m^2 \cdot hr$) was calculated. The result thereof is shown in Table 1.

Example 2

In the present example, except that 3.80 g of p-toluene sulfonic acid hydrate was used instead of benzene sulfonic acid, the water separation membrane was prepared in the same manner as example 1. The water separation membrane yielded according to the present example is composed of polypyrrole doped with p-toluene sulfonate ion of chemical formula (2).

Thereafter, except that the water separation membrane yielded according to the present example was used and 3.31 g of the ethanol water solution was supplied to the cylindrical supply member 18, the water separation performance test was performed in the same manner as example 1. The result thereof is shown in Table 1.

Example 3

In the present example, except that 4.45 g of 2,4-dimethyl benzene sulfonic acid dihydrate was used instead of benzene sulfonic acid, the water separation membrane was prepared in the same manner as example 1. The water separation membrane yielded according to the present example is composed of polypyrrole doped with 2,4-dimethyl benzene sulfonate ion of chemical formula (3).

Thereafter, except that the water separation membrane yielded according to the present example was used and 3.29 g of the ethanol water solution was supplied to the cylindrical supply member 18, the water separation performance test was performed in the same manner as example 1. The result thereof is shown in Table 1.

Example 4

In the present example, except that 4.16 g of sodium 4-ethyl benzene sulfonate was used instead of benzene sulfonic acid, the water separation membrane was prepared in the same manner as example 1. The water separation membrane yielded according to the present example is composed of polypyrrole doped with 4-ethyl benzene sulfonate ion of chemical formula (4).

Thereafter, except that the water separation membrane yielded according to the present example was used and 3.28 g of the ethanol water solution was supplied to the cylindrical supply member 18, the water separation performance test was performed in the same manner as example 1. The result thereof is shown in Table 1.

Example 5

In the present example, except that 5.23 g of 2,4,5-trichloro benzene sulfonic acid was used instead of benzene sulfonic acid, the water separation membrane was prepared in the same manner as example 1. The water separation membrane yielded according to the present example is composed of polypyrrole doped with 2,4,5-trichloro benzene sulfonate ion of chemical formula (5).

Thereafter, except that the water separation membrane yielded according to the present example was used and 3.29 g of the ethanol water solution was supplied to the cylindrical supply member 18, the water separation performance test was performed in the same manner as example 1. The result thereof is shown in Table 1.

Example 6

In the present example, except that 5.64 g of disodium 1,3-benzene di-sulfonate was used instead of benzene sulfonic acid, the water separation membrane was prepared in the same manner as example 1. The water separation membrane yielded according to the present example is composed of polypyrrole doped with 1,3-benzene di-sulfonate ion of chemical formula (6).

Thereafter, except that the water separation membrane yielded according to the present example was used and 3.26 g of the ethanol water solution was supplied to the cylindrical supply member 18, the water separation performance test was performed in the same manner as example 1. The result thereof is shown in Table 1.

Example 7

In the present example, except that 3.02 g of disodium 1,5-naphthalene di-sulfonate was used instead of benzene sulfonic acid, the water separation membrane was prepared in the same manner as example 1. The water separation membrane yielded according to the present example is composed of polypyrrole doped with 1,5-naphthalene di-sulfonate ion of chemical formula (7).

Thereafter, except that the water separation membrane yielded according to the present example was used, 3.03 g of the ethanol water solution was supplied to the cylindrical supply member 18 and the pervaporation treatment was carried out for 2.6 hrs, the water separation performance test was performed in the same manner as example 1. The result thereof is shown in Table 1.

Example 8

In the present example, except that 3.33 g of disodium 2,6-naphthalene di-sulfonate was used instead of benzene sulfonic acid, the water separation membrane was prepared in the same manner as example 1. The water separation membrane yielded according to the present example is composed of polypyrrole doped with 2,6-naphthalene di-sulfonate ion of chemical formula (8).

Thereafter, except that the water separation membrane yielded according to the present example was used, 3.33 g of the ethanol water solution was supplied to the cylindrical supply member 18 and the pervaporation treatment was carried out for 2.5 hrs, the water separation performance test was performed in the same manner as example 1. The result thereof is shown in Table 1.

Example 9

In the present example, except that 3.32 g of disodium 2,7-naphthalene di-sulfonate was used instead of benzene sulfonic acid, the water separation membrane was prepared in the same manner as example 1. The water separation membrane yielded according to the present example is composed of polypyrrole doped with 2,7-naphthalene di-sulfonate ion of chemical formula (9).

Thereafter, except that the water separation membrane yielded according to the present example was used, 3.00 g of the ethanol water solution was supplied to the cylindrical supply member 18 and the pervaporation treatment was carried out for 2.5 hrs, the water separation performance test was performed in the same manner as example 1. The result thereof is shown in Table 1.

Example 10

In the present example, except that 4.34 g of trisodium 1,3,6-naphthalene tri-sulfonate was used instead of benzene sulfonic acid, the water separation membrane was prepared in the same manner as example 1. The water separation membrane yielded according to the present example is composed of polypyrrole doped with 1,3,6-naphthalene tri-sulfonate ion of chemical formula (10).

Thereafter, except that the water separation membrane yielded according to the present example was used, 3.28 g of the ethanol water solution was supplied to the cylindrical supply member 18 and the pervaporation treatment was carried out for 2.5 hrs, the water separation performance test was performed in the same manner as example 1. The result thereof is shown in Table 1.

formance to the water separation membrane yielded according to examples 1 to 5, respectively. The water separation membrane of example 6 is doped with aromatic sulfonate ion having two sulfonate groups in benzene ring. On the other hand, the water separation membrane yielded according to examples 1 to 5, respectively, is doped with aromatic sulfonate ion having a single sulfonate group in benzene ring.

Further, it is obvious from Table 1 that the water separation membrane yielded according to examples 7 to 9, respectively, has superior water separation performance to the water separation membrane yielded according to example 6. The water separation membrane yielded according to examples 7 to 9, respectively, is doped with aromatic sulfonate ion having two sulfonate groups in naphthalene ring.

Moreover, it is obvious from Table 1 that the water separation membrane yielded according to example 10 has superior water separation performance to the water separation membrane yielded according to examples 7 to 9, respectively. The water separation membrane yielded according to example 10 is doped with aromatic sulfonate ion having three sulfonate groups in naphthalene ring.

TABLE 1

| | | | Supplied liquid | | Trapped liquid | |
| --- | --- | --- | --- | --- | --- | --- |
| | | | Before PV | After PV | After PV | |
| Example | Supplied weight (g) | Treatment time (hr) | EtOH Conc (W %) | EtOH Conc (W %) | EtOH Conc (W %) | W.P.R ($g/m^2 \cdot hr$) |
| 1 | 3.93 | 3.0 | 9.90 | 9.94 | 0.012 | 38.0 |
| 2 | 3.31 | 3.0 | 9.90 | 10.10 | <0.001 | 19.8 |
| 3 | 3.29 | 3.0 | 9.90 | 10.12 | <0.001 | 13.7 |
| 4 | 3.28 | 3.0 | 9.90 | 10.08 | <0.001 | 11.1 |
| 5 | 3.29 | 3.0 | 9.90 | 10.02 | <0.001 | 3.5 |
| 6 | 3.26 | 3.0 | 9.90 | 9.95 | <0.001 | 79.3 |
| 7 | 3.03 | 2.6 | 9.90 | 10.37 | 0.005 | 104.0 |
| 8 | 3.33 | 2.5 | 9.90 | 10.41 | 0.005 | 131.4 |
| 9 | 3.00 | 2.5 | 9.90 | 10.36 | <0.001 | 125.4 |
| 10 | 3.28 | 2.5 | 9.90 | 11.04 | <0.001 | 332.5 |

PV: Pervaporation;
EtOH: Ethanol;
W.P.R: Water permeation rate

From Table 1, it is obvious that the ethanol concentration in the cylindrical supply member 18 has been increased after pervaporation treatment by using the water separation membrane of the present invention yielded according to examples 1 to 10, respectively. In addition, it is obvious that the liquid trapped in the cold trap 13 contains almost no ethanol and is substantially water by adopting the water separation membrane of the present invention. Therefore, it is obvious that the water separation membrane of the present invention can selectively permeate water, and consequently, can be used to condense ethanol water solution.

It is also obvious from Table 1 that the water separation membrane of example 6 has superior water separation per- Example 11

In the present example, the water separation membrane was prepared in the same manner as example 10.

Thereafter, except that the ethanol concentration of the ethanol water solution supplied to the cylindrical supply member 18 was set at 95 W %, 90 W %, 50 W %, 35 W %, 9.90 W %, 1.00 W % and 0 W %, respectively, the water separation performance test was performed in the same manner as example 10. The result thereof is shown in Table 2. Note that when the ethanol concentration of the ethanol water solution is 0 W %, the ethanol water solution contains no ethanol but water only.

TABLE 2

| | | Supplied liquid | | | Trapped liquid | |
| --- | --- | --- | --- | --- | --- | --- |
| | | Before PV | | After PV | After PV | |
| Supplied Weight (g) | Treatment Time (hr) | Water Conc (W %) | EtOH Conc (W %) | EtOH Conc (W %) | EtOH Conc (W %) | W.P.R ($g/m^2 \cdot hr$) |
| 3.02 | 2.5 | 5.00 | 95.00 | 95.63 | 0.033 | 13.9 |
| 2.99 | 2.5 | 10.00 | 90.00 | 91.23 | <0.001 | 27.8 |
| 3.04 | 2.5 | 50.00 | 50.00 | 51.61 | 0.002 | 93.8 |
| 3.21 | 2.5 | 65.00 | 35.00 | 36.15 | 0.046 | 105.6 |

TABLE 2-continued

| Supplied | Treatment | Supplied liquid | | Trapped liquid | |
| | | Before PV | After PV | After PV | |
| Supplied Weight (g) | Time (hr) | Water Conc (W %) | EtOH Conc (W %) | EtOH Conc (W %) | EtOH Conc (W %) | W.P.R ($g/m^2 \cdot hr$) |
|---|---|---|---|---|---|---|
| 3.28 | 2.5 | 90.10 | 9.90 | 11.04 | <0.001 | 332.5 |
| 3.02 | 2.5 | 99.00 | 1.00 | 1.23 | 0.003 | 716.8 |
| 3.00 | 2.5 | 100.00 | 0.00 | 0.00 | 0.000 | 973.2 |

It is obvious from Table 2 that the ethanol concentration in the cylindrical supply member 18 has been increased after pervaporation treatment when the ethanol concentration of the ethanol water solution is in a range of 1 to 95 W %. In addition, it is obvious that when the ethanol concentration of the ethanol water solution is in a range of 1 to 95 W %, the lower the ethanol concentration is, the more water will be permeated. Therefore, it is obvious that the water separation membrane yielded according to example 11 can be used preferably in separating water from ethanol water solution of lower concentration.

Example 12

In the present example, the water separation membrane was prepared in the same manner as example 10.

Thereafter, except that the ethanol concentration of the ethanol water solution supplied to the cylindrical supply member 18 was set at 0.5 W %, 10 W % and 95 W %, respectively, and the pervaporation treatment was carried out for a sufficient long time, the water separation performance test was performed in the same manner as example 10. The result thereof is shown in Table 3.

TABLE 3

| Supplied | | Supplied liquid | | Trapped liquid | |
| | | Before PV | | After PV | |
| Supplied Weight (g) | Treatment Time (hr) | EtOH Conc (W %) | After PV EtOH Conc (W %) | EtOH Conc (W %) | W.P.R ($g/m^2 \cdot hr$) |
|---|---|---|---|---|---|
| 5.5 | 45.3 | 0.5 | 99.01 | 0.09 | 669.8 |
| 3.5 | 96.0 | 10.00 | 99.50 | 1.29 | 95.7 |
| 0.47 | 24.0 | 95.00 | 99.46 | 0.61 | 3.1 |

It is obvious from Table 3 that the ethanol concentration of the ethanol water solution remained in the cylindrical supply member 18 can be concentrated to at least 99 W % after the pervaporation treatment has been performed for a sufficiently long time, regardless of the ethanol concentration of the ethanol water concentration. Therefore, it is obvious that the ethanol water solution of a lower concentration can be condensed in one step according to the pervaporation method by using the water separation membrane yielded from example 12 to yield the ethanol water solution of at least 99 W %.

Example 13

In the present example, the water separation membrane was prepared in the same manner as example 10.

Thereafter, except that in the pervaporation treatment by using the water separation membrane prepared in the present example, when the degree of vacuum of the vacuum indicator dropped to 500 Pa or less after the vacuum pump was actuated, the vacuum pump was stopped and the degree of vacuum was maintained in a given range, the water separation performance test was performed in the same manner as example 10. The result thereof is shown in Table 4.

TABLE 4

| | | | Supplied liquid | | Trapped liquid | |
| | | Supplied | Before PV | After PV | After PV | |
| Example | Vacuum pump | Weight (g) | EtOH Conc (W %) | EtOH Conc (W %) | EtOH Conc (W %) | W.P.R ($g/m^2 \cdot hr$) |
|---|---|---|---|---|---|---|
| 10 | Remained at ON | 3.3 | 9.9 | 11.04 | <0.01 | 332.5 |
| 13 | ON to OFF, remained at OFF | 3.1 | 9.9 | 10.90 | 0.032 | 276.8 |

It is obvious from Table 4 that the water separation performance can be yielded in example 13 in a similar degree to that in example 10. In example 13, in the pervaporation treatment, when the degree of vacuum dropped to 500 Pa or less, the vacuum pump was stopped and the degree of vacuum was maintained at a given range. On the other hand, in example 10, the vacuum pump was maintained at working in the pervaporation treatment. Therefore, according to the water separation membrane of the present invention, if the degree of vacuum can be maintained at a given range in the pervaporation treatment, it is acceptable to stop the vacuum pump so as to save energy.

Example 14

In the present example, the water separation membrane was prepared in the same manner as example 10.

Thereafter, except that 6 to 20 g of 5 W % saccharide water solution was used instead of the ethanol water solution, respectively, the water separation performance test was performed in the same manner as example 10. The result thereof is shown in Table 5. Note that the saccharide water solution includes water solution of glucose, xylose or the like.

TABLE 5

| Supplied Weight (g) | Treatment Time (hr) | Supplied liquid Before PV Saccharide Conc (W %) | After PV Saccharide Conc (W %) | Trapped liquid After PV Saccharide Conc (W %) | W.P.R (g/m² · hr) |
|---|---|---|---|---|---|
| 19.6 | 48.0 | 5 | 15.3 | 0 | 716.5 |
| 6.3 | 14.4 | 5 | 18.9 | 0 | 859.5 |
| 19.7 | 110.0 | 5 | 24.1 | 0 | 383.5 |

From Table 5, it is obvious that the saccharide concentration in the cylindrical supply member 18 has been increased after pervaporation treatment by using the water separation membrane of the present example. Moreover, according to the water separation membrane of the present example, it is obvious that the liquid trapped in the cold trap 13 contains no saccharide at all. Therefore, it is obvious that the water separation membrane of the present invention can selectively permeate water, and consequently, can be used to condense not only ethanol water solution but also saccharide water solution.

Example 15

In the present example, firstly, ion-exchanged water is deoxidized by blowing argon gas therein. Next, a polymerization solution is prepared by dissolving 5.20 g of 25 W % sodium vinyl sulfonate water solution and then 0.67 g of pyrrole in 100 ml of the deoxidized ion-exchanged water. In the polymerization solution, the concentration of vinyl sulfonate ion is 0.1 mol/L and the concentration of pyrrole is 0.1 mol/L.

Next, the polymerization solution prepared according to the present example was put into the polymerization container 2 of the electrochemical polymerization device 1 as illustrated in FIG. 1. The working electrode 3 was set as an anode and the counter electrodes 4 and 4 were set as a cathode, and the constant-current oxidative polymerization was performed at a current density of 0.4 mA/cm² for 1.5 hrs to yield a membrane of a thickness of roughly 21 µm on both surfaces of the working electrode 3, respectively. Thereafter, the water separation membrane composed of polypyrrole doped with vinyl sulfonate ion of chemical formula (11) was yielded by detaching the membranes from the working electrode 3.

Thereafter, except that the water separation membrane yielded according to the present example was used, 2.20 g of 9.90 W % ethanol water solution was supplied to the cylindrical supply member 18 and the pervaporation treatment was carried out at room temperature (25° C.) for 2 hrs, the water separation performance test was performed in the same manner as example 1. The result thereof is shown in Table 6.

Example 16

In the present example, except that 5.20 g of 25 W % sodium polyvinyl sulfonate water solution was used instead of sodium vinyl sulfonate water solution, the water separation membrane was prepared in the same manner as example 15. The water separation membrane yielded according to the present example is composed of polypyrrole doped with polyvinyl sulfonate ion of chemical formula (12).

Thereafter, except that the water separation membrane yielded according to the present example was used, 3.31 g of the ethanol water solution was supplied to the cylindrical supply member 18 and the pervaporation treatment was carried out for 0.5 hrs, the water separation performance test was performed in the same manner as example 1. The result thereof is shown in Table 6.

TABLE 6

| Example | Supplied EtOH (g) | Treatment Time (hr) | Supplied liquid Before PV EtOH (W %) | After PV EtOH (W %) | Trapped liquid After PV EtOH (W %) | W.P.R (g/m² · hr) |
|---|---|---|---|---|---|---|
| 15 | 2.20 | 2.0 | 9.90 | 11.77 | 0.038 | 143.1 |
| 16 | 3.31 | 0.5 | 9.90 | 12.54 | <0.001 | 809.6 |

From Table 6, it is obvious that the ethanol concentration in the cylindrical supply member 18 has been increased after pervaporation treatment by using the water separation membrane of the present invention yielded according to examples 15 and 16, respectively. In addition, it is obvious that the liquid trapped in the cold trap 13 contains almost no ethanol and is substantially water by adopting the water separation membrane of the present invention. Therefore, it is obvious that the water separation membrane of the present invention can selectively permeate water, and consequently, can be used to condense ethanol water solution.

Furthermore, from Table 6, it is obvious that the water separation membrane yielded according to example 16 can permeate more water in a short time and has superior water separation performance to that yielded according to example 15. The water separation membrane of example 16 is doped with polyvinyl sulfonate ion. On the other hand, the water separation membrane of example 15 is doped with vinyl sulfonate ion.

What is claimed is:

1. A water separation membrane composed of a polypyrrole doped with an aromatic sulfonate ion that has a naphthalene ring, wherein the aromatic sulfonate ion is trisodium 1,3,6-naphthalene tri-sulfonate.

2. A water separation membrane composed of a polypyrrole doped with an aromatic sulfonate ion that has a naphthalene ring, wherein the aromatic sulfonate ion has at least two ionized sulfonic groups.

3. A water separation membrane composed of a polypyrrole doped with an aromatic sulfonate ion that has a naphthalene ring, wherein the aromatic sulfonate ion has at least three ionized sulfonic groups.

* * * * *